United States Patent
Bindell et al.

(10) Patent No.: US 6,362,475 B1
(45) Date of Patent: Mar. 26, 2002

(54) SCANNING ELECTRON MICROSCOPE/ ENERGY DISPERSIVE SPECTROSCOPY SAMPLE PREPARATION METHOD AND SAMPLE PRODUCED THEREBY

(75) Inventors: Jeffrey B. Bindell; Frederick A. Stevie; Catherine Vartuli, all of Orlando, FL (US)

(73) Assignee: Agere Systems Guardian Corp., Orlando, FL (US)

( * ) Notice: Subject to any disclaimer, the term of this patent is extended or adjusted under 35 U.S.C. 154(b) by 0 days.

(21) Appl. No.: 09/337,966

(22) Filed: Jun. 22, 1999

(51) Int. Cl.[7] .............................. G01N 1/28; G01N 1/32; H01J 37/20
(52) U.S. Cl. ................... 250/307; 250/309; 250/310; 250/492.21; 250/492.2; 438/690; 438/691
(58) Field of Search ................... 250/307, 309, 250/310, 492.21, 492.2; 438/690, 691

(56) References Cited

U.S. PATENT DOCUMENTS

| 5,656,811 | A | * | 8/1997 | Itoh et al. ................... 250/309 |
| 5,993,291 | A | * | 11/1999 | Tsai et al. ...................... 451/28 |
| 6,140,603 | A | * | 10/2000 | Hwang et al. ......... 219/121.69 |

* cited by examiner

Primary Examiner—Bruce Anderson
Assistant Examiner—Nikita Wells (57) ABSTRACT

A method of preparing a monolithic structure for scanning electron microscope/energy dispersive spectroscopy (SEM/EDS) and a sample produced by way of the method. In one embodiment, the method includes: (1) aiming a focused ion beam at a location behind or beneath an area of interest in the monolithic structure and (2) employing the focused ion beam to remove at least a portion of an interaction volume of material beneath the area of interest. The area of interest preferably remains substantially intact for the spectroscopy.

20 Claims, 10 Drawing Sheets

SCANNING ELECTRON MICROSCOPE/ ENERGY DISPERSIVE SPECTROSCOPY SAMPLE PREPARATION METHOD AND SAMPLE PRODUCED THEREBY

TECHNICAL FIELD OF THE INVENTION

The present invention is directed, in general, to analysis of monolithic structures and, more specifically, to a scanning electron microscope/energy dispersive spectroscopy (SEM/EDS) sample preparation method and a monolithic sample produced by way of the method.

BACKGROUND OF THE INVENTION

In semiconductor processing today it is often necessary to spectroscopically examine portions of a semiconductor die to determine the results of new or conventional processes. The examination may be to confirm the results of an experimental process, or even to determine the nature of a particular failure or defect in a semiconductor device. Of course, because of the nature of integrated circuits, the examination must often be performed on samples cut from the die in question. Scanning electron microscopy/energy dispersive spectroscopy (SEM/EDS) is frequently used in the determination of the composition of target material in a feature of a semiconductor die. In SEM/EDS, X-rays generated by the primary electron beam's interaction with the target assist in determining the composition of the target.

Figure 1:
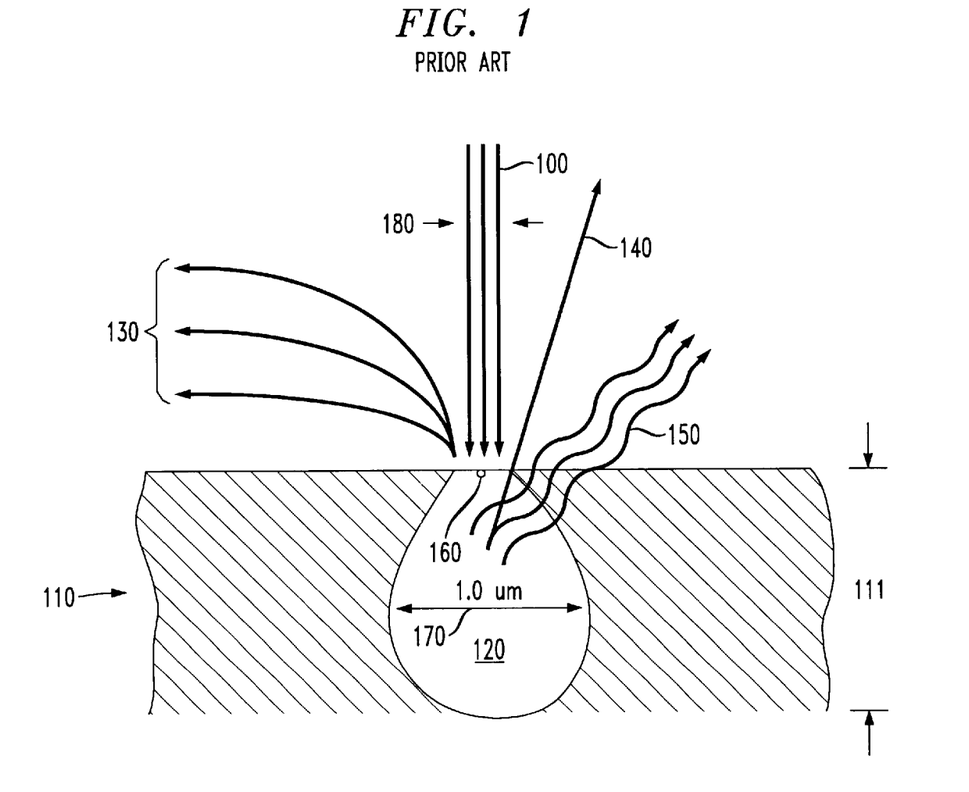
FIG. 1 illustrates a cross-sectional view of a conventional SEM sample symbolically showing effects of the SEM process.

Referring initially to FIG. 1, illustrated is a cross-sectional view of a conventional SEM sample symbolically showing effects of the SEM process. A primary electron beam 100 with width 180 is directed to a sample 110 having a thickness 111. The sample 110 may be cut from any orientation within a material of interest. In this embodiment, the beam 100 has a width 180 and a tear shaped interaction volume 120, with depth 160. For example, at a given beam energy and in a given material, a beam width 180 of 10 nm can produce an interaction volume with a maximum width 170 of 1 $\mu$m. The beam 100 interacts with essentially all of the material in the interaction volume 120, producing secondary electrons 130, backscattered electrons 140, and X-rays 150. The specific X-rays present in the spectra are traceable by EDS to particular elements present at the site of the SEM examination.

As device sizes are made ever smaller, a defect that was insignificant in the past becomes quite significant. However, as the semiconductor features and defects become smaller, it has become increasingly difficult to obtain the lateral resolution needed from EDS for compositional identification of small defects and thin layers. With a decrease in feature size, the feature becomes a smaller percentage of the target, thereby reducing the X-ray emanations from the feature. It is well known that the interaction volume 120 depth 160 and width 170 are dependent upon the accelerating energy of the primary electron beam 100. However, because the beam 100 interacts with the entire interaction volume 120, precise data on the nature of a feature of interest 160 at the examination site may be unclear. In order to reduce the interaction volume, the primary beam accelerating voltage has been reduced to account for the reduced feature size. However, several elements commonly used in semiconductor fabrication have overlapping peaks at lower beam energies, and the ability to distinguish between the elements is therefore lost at these low beam energies. At higher beam voltages more peaks in the EDS spectra allow for better discrimination between the elements present. Therefore, reducing beam energy does not effectively improve element discrimination.

Of course, tool manufacturers have worked to improve the sensitivity of their tools. Unfortunately, these efforts have met with limited success, and the available sensitivity is still not sufficient for current and projected needs.

Figure 2A:
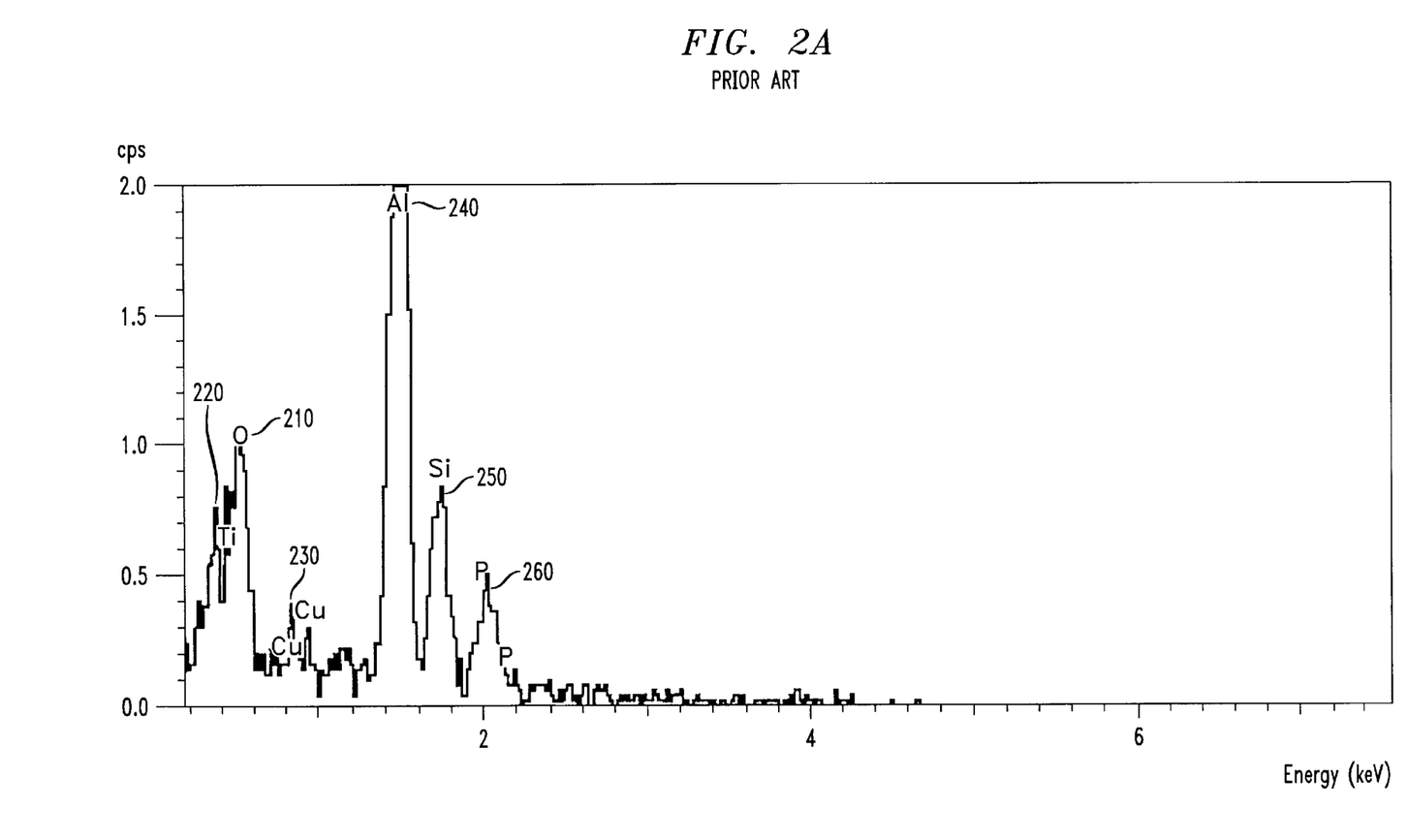
FIG. 2A illustrates EDS spectra of a conventional semiconductor SEM sample taken with an incident electron beam of 5 keV.
Figure 2B:
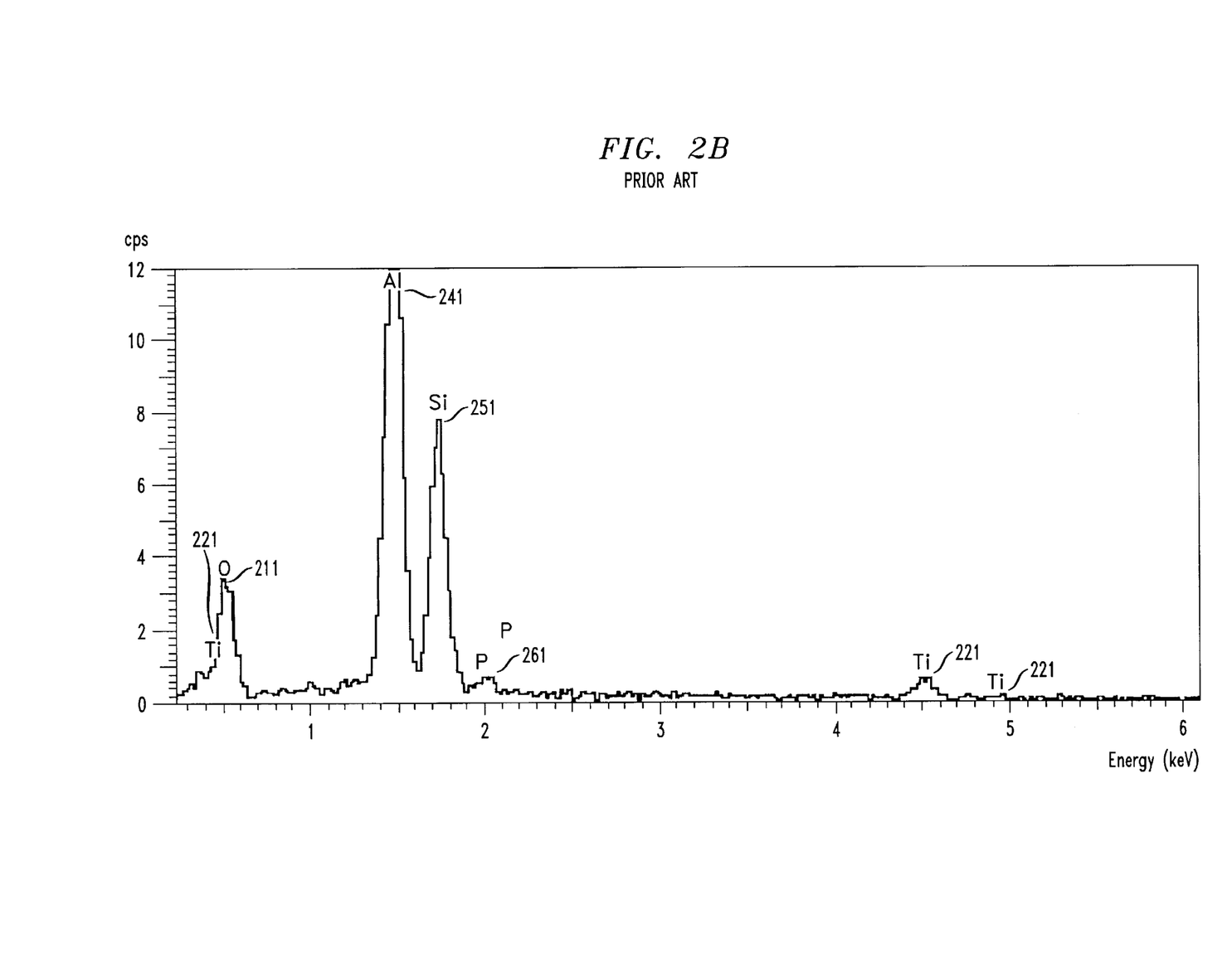
FIG. 2B illustrates EDS spectra of the same area as shown in FIG. 2A with an incident electron beam of 10 keV.

Referring now to FIG. 2A, illustrated are EDS spectra of a conventional semiconductor SEM sample taken with an incident electron beam of 5 keV. As can be seen, the results make it difficult to resolve between oxygen 210 and titanium 220. There also appears to be copper 230 present, as well as aluminum 240, silicon 250 and phosphorous 260. Referring now to FIG. 2B, illustrated are EDS spectra of the same area as shown in FIG. 2A with an incident electron beam of 10 keV. Comparing FIG. 2B to FIG. 2A, it is clear that oxygen 211, titanium 221, aluminum 241, silicon 251 and phosphorus 261 are all present. It is also now evident that copper is not present. It is readily apparent that the definition of the peaks 211, 221, 241, 251, 261 is much better at the higher (10 keV) beam energy.

Figure 3A:
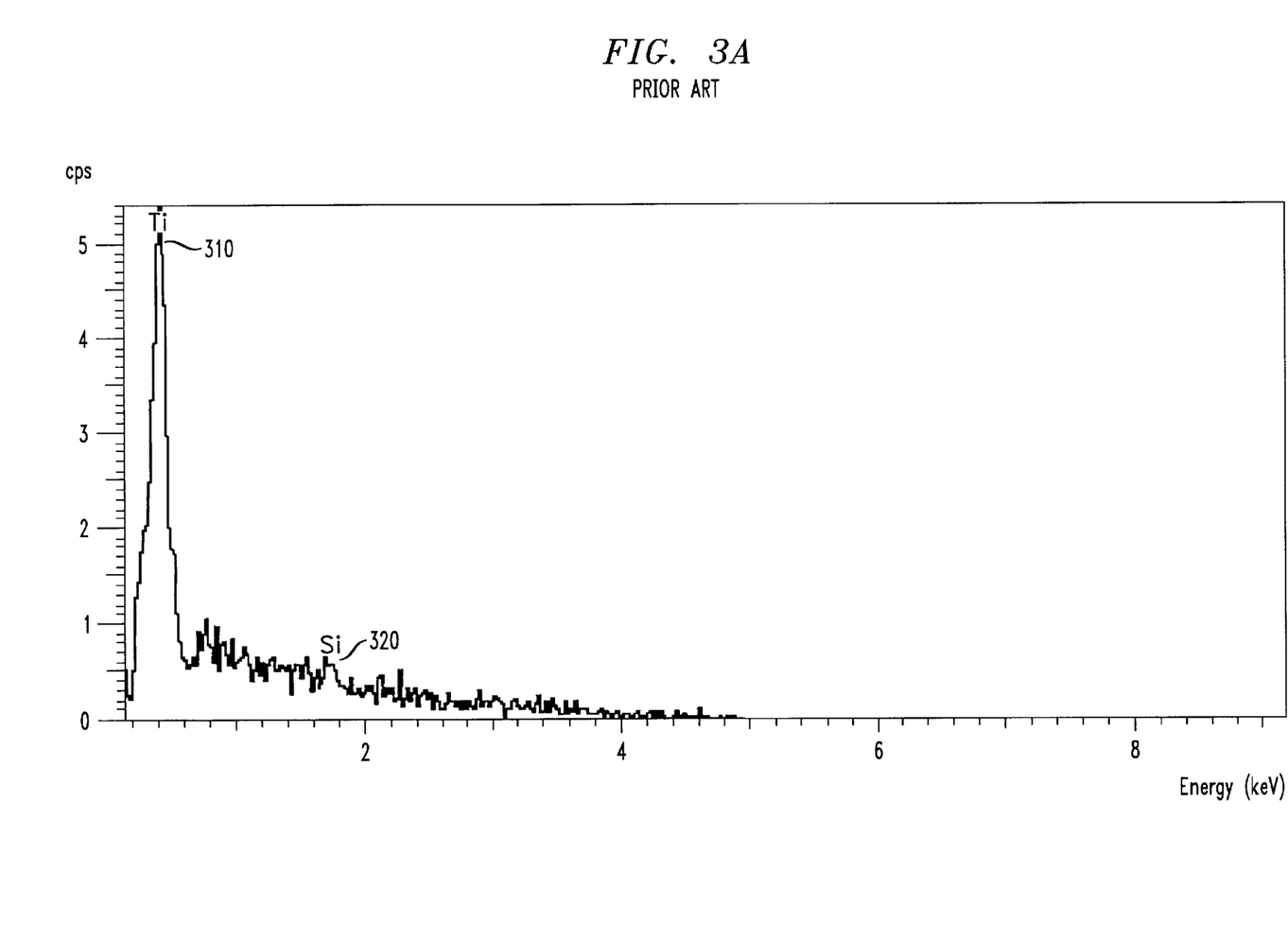
FIG. 3A illustrates EDS spectra taken at 5 keV of a different semiconductor SEM sample.
Figure 3B:
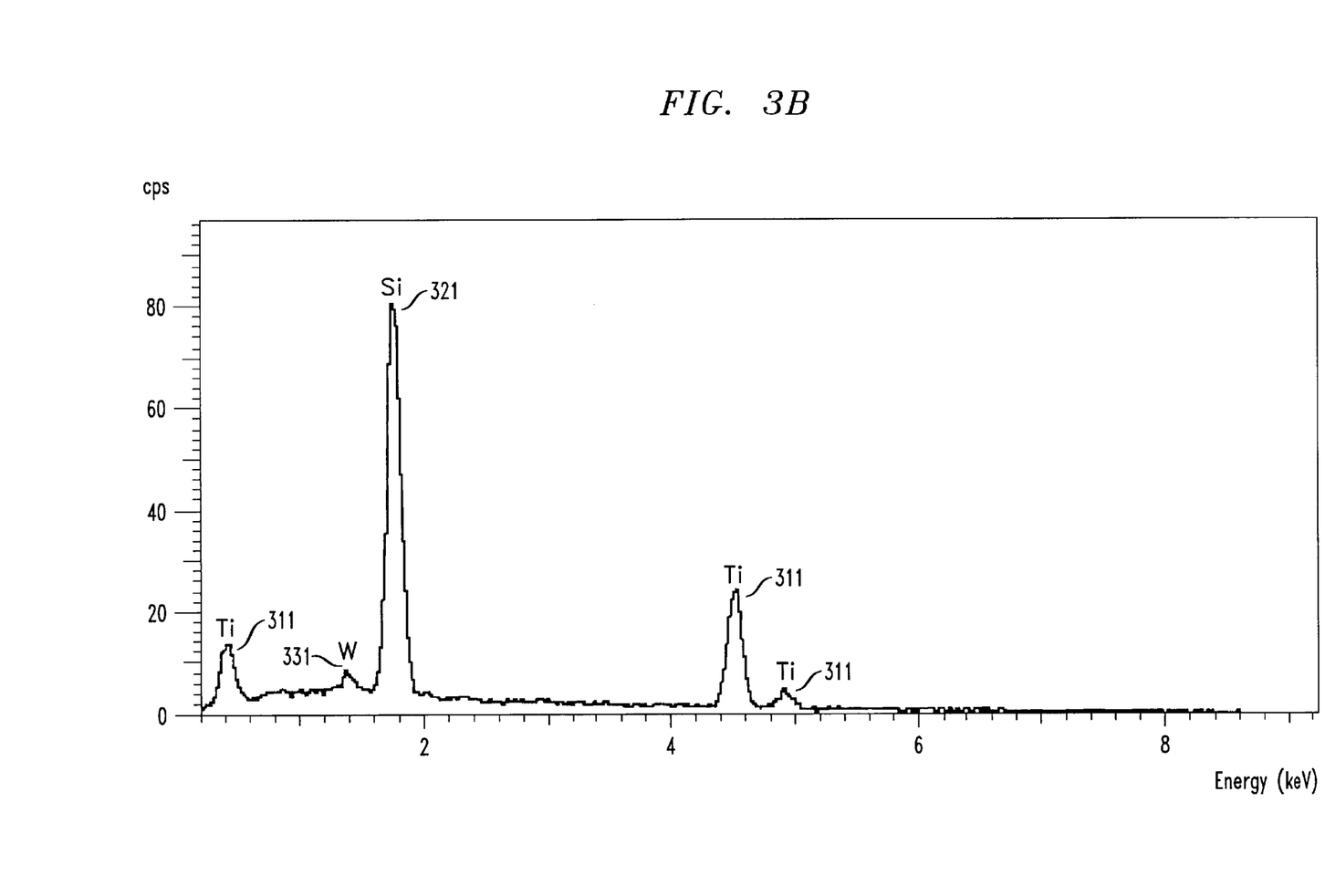
FIG. 3B illustrates EDS spectra taken at 10 keV of the same area as shown in FIG. 3A.

Referring now to FIG. 3A, illustrated are EDS spectra taken at 5 keV of a different semiconductor SEM sample. At this voltage, titanium 310 and possibly silicon 320 appear to be present. However, one who is skilled in the art will readily observe because of the relative magnitudes of the peaks at X-ray energy levels of 0.6 keV and above that it is extremely difficult to discern the presence of any particular element. Referring now to FIG. 3B, illustrated are EDS spectra taken at 10 keV of the same area as shown in FIG. 3A. One who is skilled in the art will readily appreciate that the spectra of FIG. 3B clearly allows one to differentiate peaks associated with titanium 311, silicon 321, and tungsten 331. Comparing FIG. 3B to FIG. 3A, one can readily understand that the presence of tungsten is simply not recognizable from the spectra of FIG. 3A. Thus higher beam energies make identification of elements much easier.

Accordingly, what is needed in the art is a sample preparation method that minimizes the interaction volume while retaining the feature of interest.

SUMMARY OF THE INVENTION

To address the above-discussed deficiencies of the prior art, the present invention provides a method of preparing a monolithic structure for scanning electron microscope/energy dispersive spectroscopy (SEM/EDS) and a sample produced by way of the method. In one embodiment, the method includes: (1) aiming a focused ion beam at any location beneath an area of interest of any size or depth in the monolithic structure and (2) employing the focused ion beam to remove at least a portion of an interaction volume of material beneath the area of interest. The area of interest preferably remains substantially intact for the subsequent spectroscopy.

The present invention therefore introduces the broad concept of employing a focused ion beam to remove at least some of the interaction volume beneath an area of interest that would otherwise generate unwanted background noise during subsequent SEM/EDS analysis. For purposes of the present invention, a "monolithic structure" is defined as a structure formed in or on a body of material. A monolithic structure may be a semiconductor wafer (such as a silicon or gallium arsenide wafer), but can be composed of any material. For purposes of the present invention, an "area of interest" is defined as any portion of the monolithic structure that is to be the subject of analysis.

In one embodiment of the present invention, the area of interest is a portion of a surface of the monolithic structure. Alternatively, the area of interest could be located above or below the surface of the monolithic structure.

A preferred embodiment of the present invention comprises employing the focused ion beam to remove an entirety of the interaction volume. Of course, removal of only a portion of the interaction volume may be advantageous in some applications.

In one embodiment of the present invention, the employing comprises employing the focused ion beam to remove at least the portion of the interaction volume such that the area of interest becomes membranous. The membranous area of interest may, but need not, have a thickness comparable to samples employed in conventional transmission electron microscope (TEM)/EDS analysis.

In one embodiment of the present invention, the monolithic structure comprises a silicon wafer. Alternatively, the monolithic structure could be a gallium arsenide wafer or a wafer or body of another suitable composition.

In one embodiment of the present invention, the monolithic structure comprises at least one layer located on a silicon substrate. Alternatively, the monolithic structure could comprise a layer formed within the silicon substrate, or the substrate itself.

In one embodiment of the present invention, the method further includes performing the energy dispersive spectroscopy on the area of interest at an energy greater than 5 keV. In an embodiment to be illustrated and described, the energy dispersive spectroscopy is performed at an energy of about 10 keV. Those skilled in the pertinent art will understand, however, that the present invention is not limited to a particular energy level or range thereof.

The foregoing has outlined, rather broadly, preferred and alternative features of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention. Those skilled in the art should also realize that such equivalent constructions do not depart from the spirit and scope of the invention in its broadest form.

BRIEF DESCRIPTION OF THE DRAWINGS

For a more complete understanding of the present invention, reference is now made to the following descriptions taken in conjunction with the accompanying drawings, in which.

DETAILED DESCRIPTION

Figure 4:
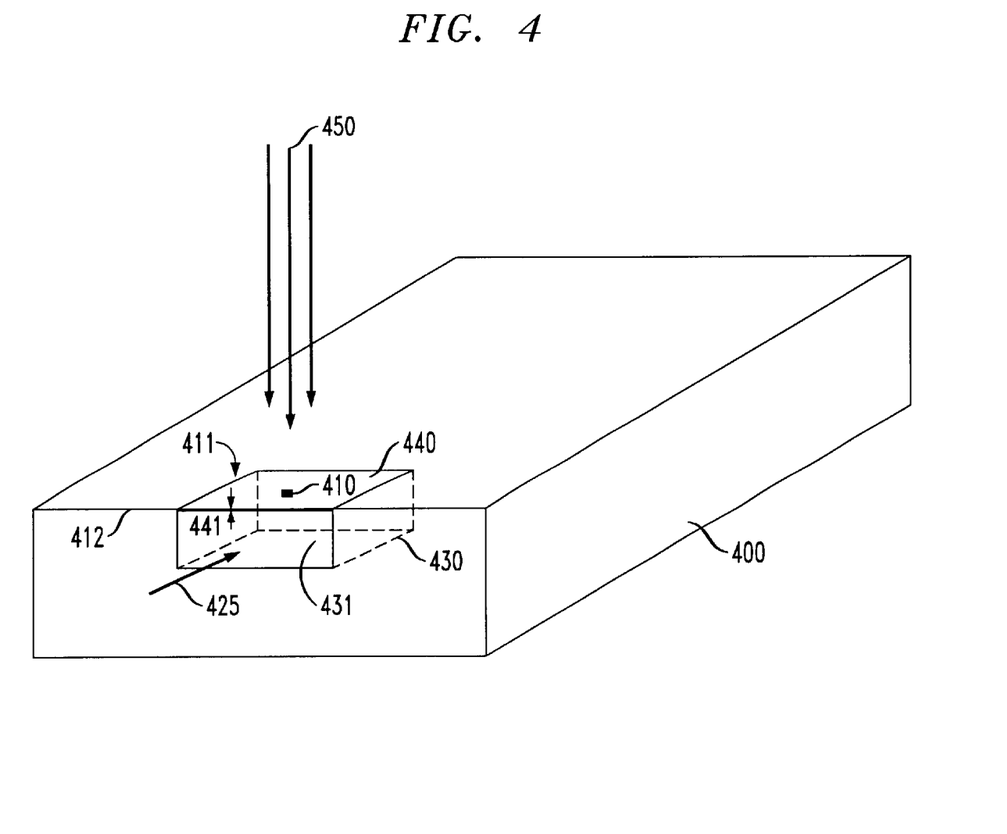
FIG. 4 illustrates an isometric view of a semiconductor die having a feature of interest.

Referring now to FIG. 4, illustrated is an isometric view of a semiconductor die 400 having a feature of interest 410. In the present case, the feature of interest 410 is located on a surface 411 of the die 400. The die 400 may be a monolithic structure as is common in semiconductor manufacturing and may be at the semiconductor wafer stage, or any subsequent stage wherein one or more layers of material has been deposited on the substrate. The die 400 has been initially prepared by cutting so that the feature of interest 410 is proximate an edge 412 of the die 400. Of course, if the feature of interest 410 is initially located within the die 400, it may be necessary to cut the die 400 so as to expose the feature of interest 410. One who is skilled in the art is familiar with methods for cutting and polishing semiconductor dies to a prescribed depth.

Using a focused ion beam (FIB) 425, a volume 430 of material (removal volume) is cut from the die 400 beneath the feature of interest 410 creating a cavity 431 and forming a sample 440. The use of the term "beneath" is relative to the position of the feature of interest 410 when placed for examination by SEM/EDS. The removal volume 430 is all of but the surface of what would have constituted an interaction volume 120 as in FIG. 1 if it were still present when the feature 410 is examined with SEM/EDS. By eliminating the removal volume 430, a primary electron beam 450 cannot interact with the material removed. A thickness 441 of the sample 440 is such that it may be considered to be membranous, or electron transparent. The feature 410 may, depending upon the tool capabilities, be examined as it remains attached to the die 400. Alternatively, the sample 440 may be cut free from the die 400 and mounted for examination. Alternatively, the FIB beam 425 and the primary electron beam 450 can be interchanged so the material is removed from behind rather than beneath the feature of interest.

Figure 5:
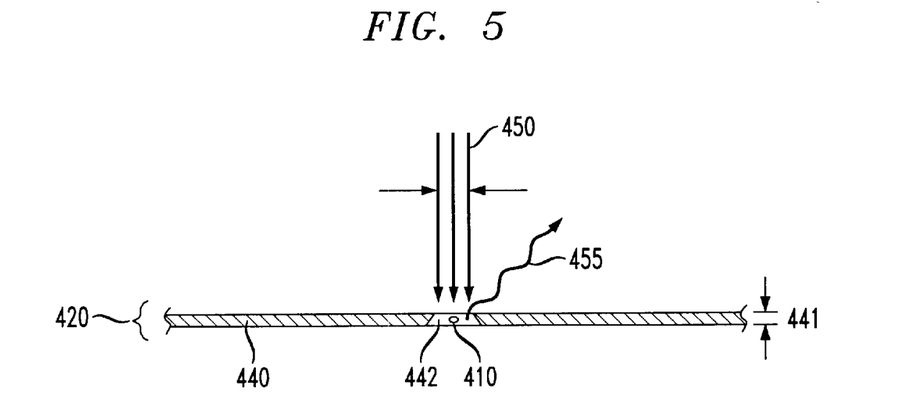
FIG. 5 illustrates a sectional view of the SEM sample of FIG. 4 symbolically showing the effects of the SEM/EDS process.

Referring now to FIG. 5, illustrated is a sectional view of the SEM sample of FIG. 4 symbolically showing the effects of the SEM/EDS process. The primary electron beam 450 of about 10 nm in width and greater than 5 keV is directed to the sample 440 having thickness 441. As can be seen, the beam 450 has an interaction volume 420 that is significantly less than (perhaps only 5 percent of) the SEM interaction volume 120 of FIG. 1. As a result, of the smaller interaction volume 420, secondary emission of electrons, backscattered electrons and X-rays 455 are essentially eliminated except for those occurring in the feature of interest 410. Because there is no material below the sample 440, higher beam energies, e.g., $\geq 10$ keV, may be used. Therefore, better test results, including improved lateral resolution, are available using these thinned samples and higher beam energies. As can be seen by comparing FIG. 1 to FIG. 5, the difference in sample thicknesses (111 vs. 441) between SEM and thinned samples is significant.

Figure 6A:
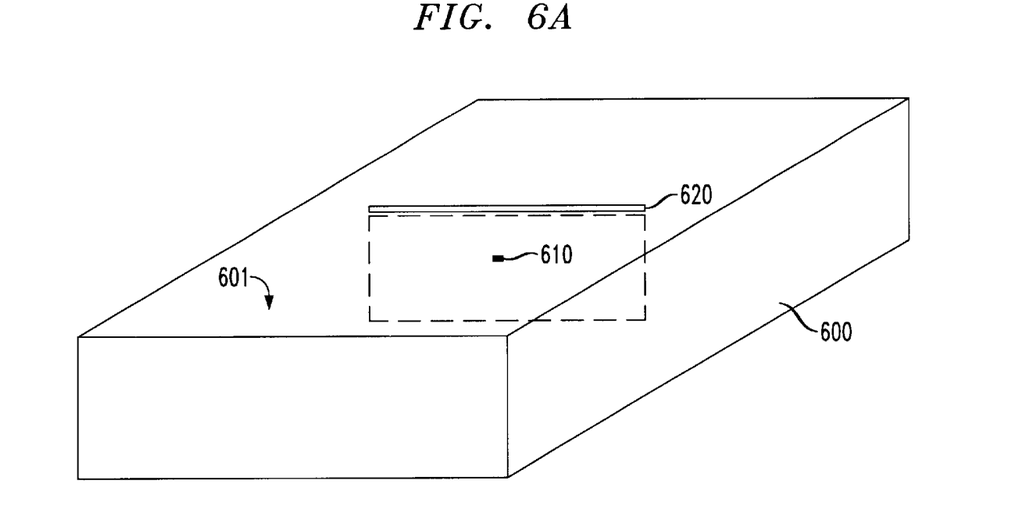
FIG. 6A illustrates an isometric view of a semiconductor die with an embedded feature of interest to be sampled by an alternative embodiment of the present invention.
Figure 6B:
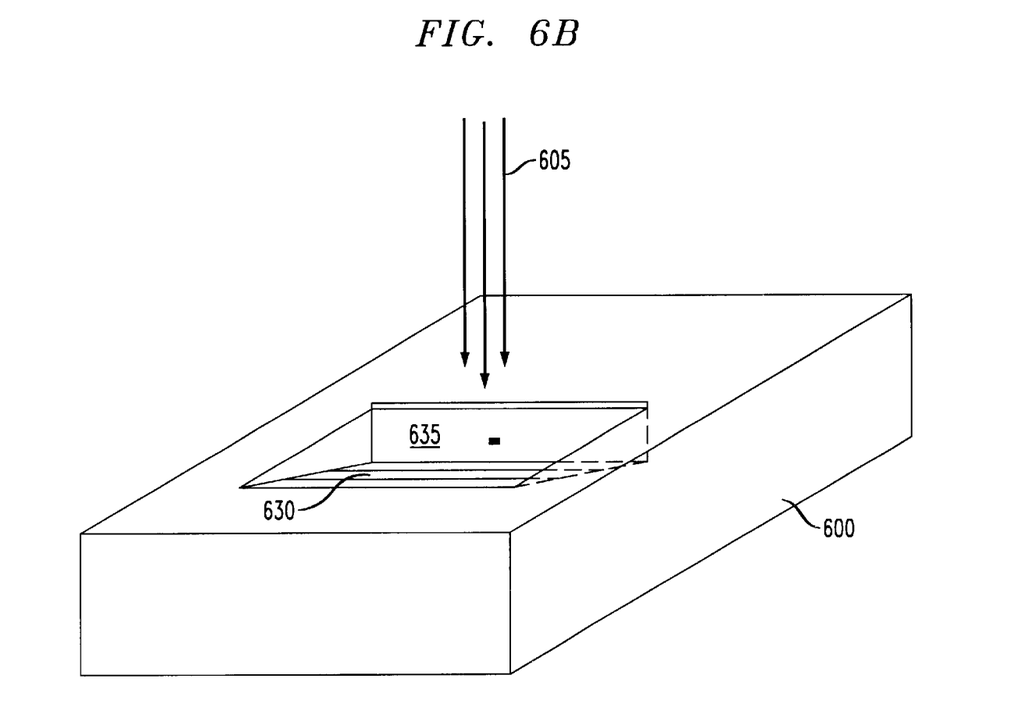
FIG. 6B illustrates the semiconductor die of FIG. 6A with a stair step trench cut in the top surface.
Figure 6C:
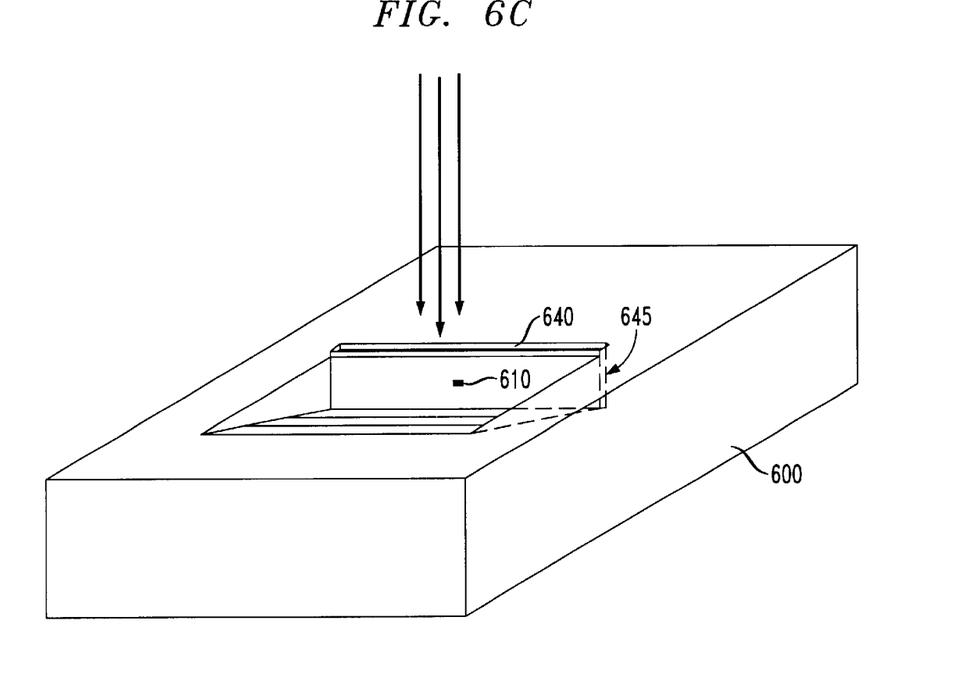
FIG. 6C illustrates the semiconductor die of FIG. 6B with a small, parallelepiped-shaped trench cut in the die to form a rear face of the feature.
Figure 6D:
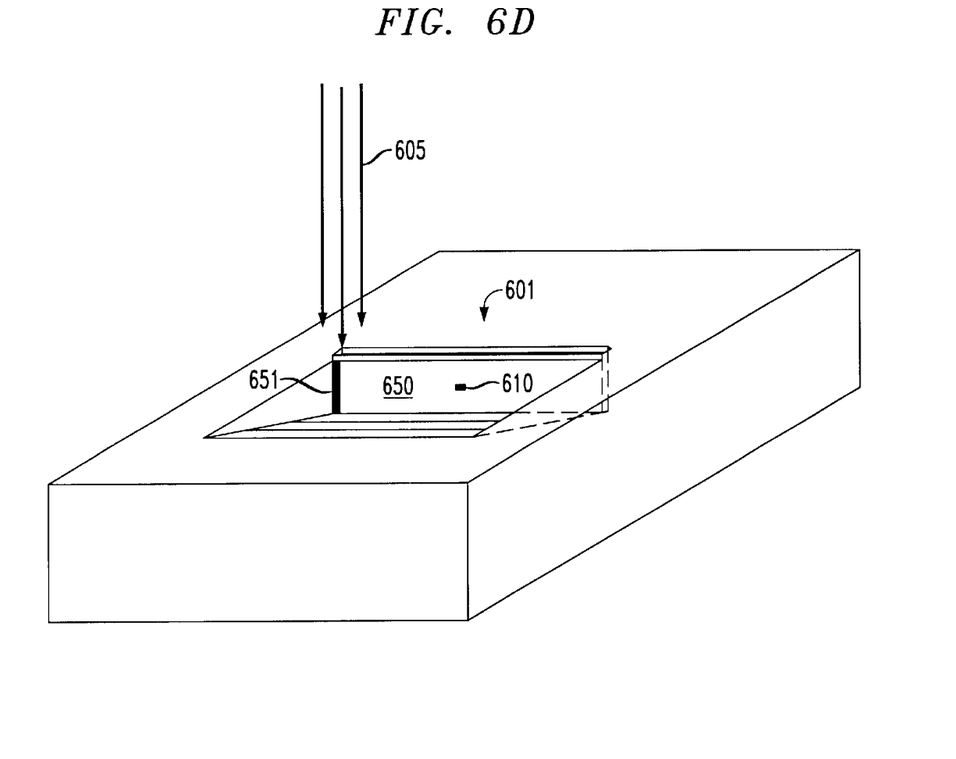
FIG. 6D illustrates the semiconductor die of FIG. 6C with the feature of interest on what is now identifiable as a sample.
Figure 6E:
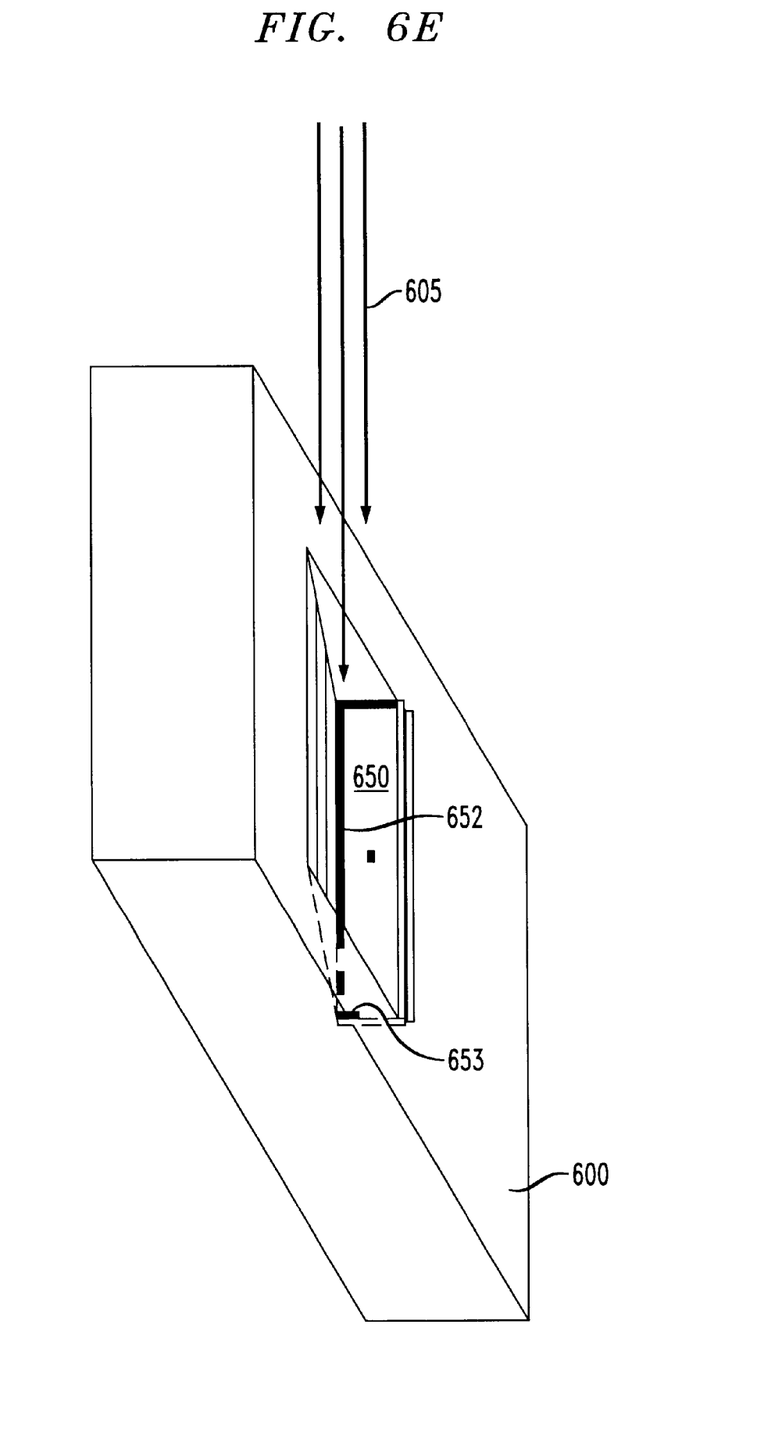
FIG. 6E illustrates the semiconductor die of FIG. 6D tilted to permit the FIB to cut part way up a second side.
Figure 6F:
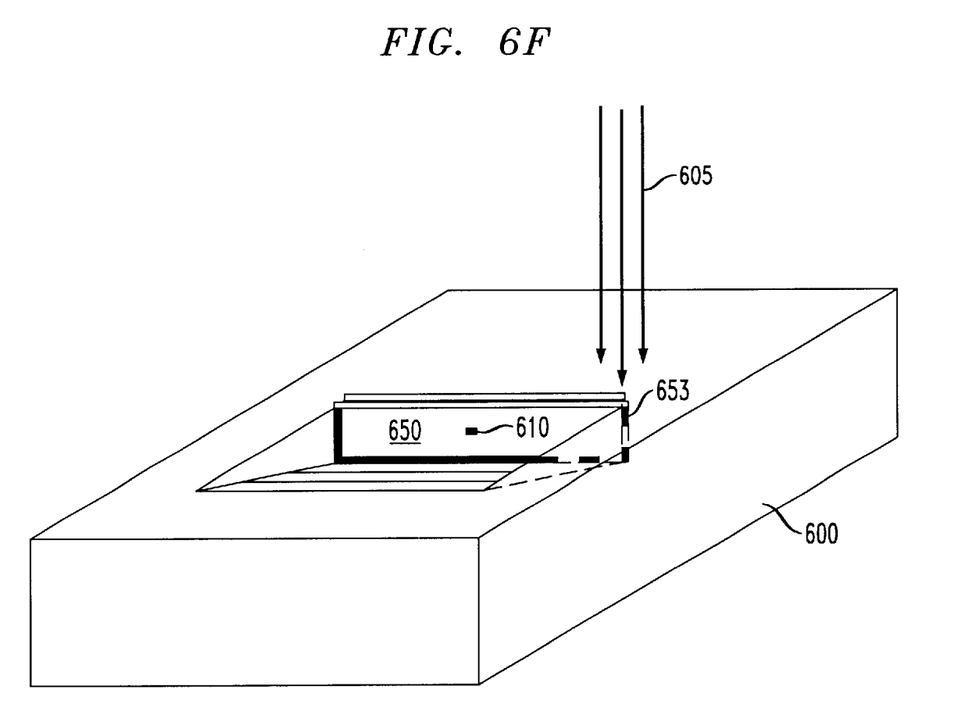
FIG. 6F illustrates the semiconductor die of FIG. 6E returned to an erect position for further thinning of the sample and cutting through the second side.

Referring now to FIG. 6A, illustrated is an isometric view of a semiconductor die 600 with an embedded feature of interest 610 to be sampled by an alternative embodiment of the present invention. In this instance, the feature of interest 610 is embedded in the die 600 rather than on an exposed surface 601. The semiconductor die 600 is initially prepared by having a layer of metal 620 deposited on the surface 601 of the die 600 to protect the surface 601. Using a FIB 605, a stair step or sloped trench 630 is cut in the surface 601 up to a front face 635 of the feature 610 as is shown in FIG. 6B. FIG. 6C shows the semiconductor die 600 of FIG. 6B with a small, parallelepiped-shaped trench 640 cut in the die 600 to form a rear face 645 of the feature 610. FIG. 6D shows the feature 610 on what is now identifiable as a sample 650 having been further thinned with the FIB 605 and one side 651 cut through from the top surface 601. In FIG. 6E, the die 600 is tilted to permit the FIB 605 to undercut the sample 650 at its base 652, and part way up a second side 653. In FIG. 6F, the die 600 has been returned to its erect position for further thinning of the sample 650 and cutting through the second side 653. The sample 650 may then be removed by a micromanipulator (not shown) and mounted for examination. Examination of the sample 650 and feature 610 is by conventional SEM/EDS methods. However, these FIB lift-out samples may also be used in TEM, AFM, AES and SIMS systems.

Therefore, methods have been described for the preparation of samples from a semiconductor die using focused ion beam technology to create electron transparent specimens. The removal of essentially all of the interaction volume below a feature of interest eliminates extraneous X-rays from occurring and clouding EDS examination. The method may be used to prepare semiconductor die samples at any stage of semiconductor manufacturing.

Although the present invention has been described in detail, those skilled in the art should understand that they can make various changes, substitutions and alterations herein without departing from the spirit and scope of the invention in its broadest form.

What is claimed is:

1. A method of preparing a monolithic structure for scanning electron microscope/energy dispersive spectroscopy, comprising:

aiming a focused ion beam at a location behind an area of interest in said monolithic structure; and employing said focused ion beam to remove an interaction volume of said monolithic structure, to form a cavity in said monolithic structure behind said area of interest, to form a test sample containing said area of interest and said cavity.

2. The method as recited in claim 1 wherein said area of interest is a portion of a surface of said monolithic structure.

3. The method as recited in claim 1 wherein said employing comprises employing said focused ion beam to remove an entirety of said interaction volume.

4. The method as recited in claim 1 wherein said employing comprises employing said focused ion beam to remove at least said portion of said interaction volume such that said area of interest becomes membranous.

5. The method as recited in claim 1 wherein said monolithic structure comprises a silicon wafer.

6. The method as recited in claim 1 wherein said monolithic structure comprises at least one layer located on a silicon substrate.

7. The method as recited in claim 1 further comprising performing said energy dispersive spectroscopy on said area of interest at an energy greater than 5 keV.

8. A scanning electron microscope/energy dispersive spectroscopy sample, comprising:

a monolithic structure having a cavity therein, said cavity being devoid of an interaction volume of material; and an area of interest in front of said cavity.

9. The sample as recited in claim 8 wherein said area of interest is a portion of a surface of said monolithic structure.

10. The sample as recited in claim 8 wherein said cavity encompasses an entirety of said interaction volume.

11. The sample as recited in claim 8 wherein said area of interest is membranous.

12. The sample as recited in claim 8 wherein said monolithic structure comprises a silicon wafer.

13. The sample as recited in claim 8 wherein said monolithic structure comprises at least one layer located on a silicon substrate.

14. A method of performing scanning electron microscope/energy dispersive spectroscopy on a semiconductor wafer, comprising:

aiming a focused ion beam at a location behind an area of interest in said semiconductor wafer;

employing said focused ion beam to remove an interaction volume of said semiconductor wafer, to form a cavity in said semiconductor wafer behind said area of interest, to form a test sample containing said area of interest and said cavity; and performing said energy dispersive spectroscopy on said area of interest at an energy greater than 5 keV.

15. The method as recited in claim 14 wherein said area of interest is a portion of a surface of said semiconductor wafer.

16. The method as recited in claim 14 wherein said employing comprises employing said focused ion beam to remove an entirety of said interaction volume.

17. The method as recited in claim 14 wherein said employing comprises employing said focused ion beam to remove at least said portion of said interaction volume such that said area of interest becomes membranous.

18. The method as recited in claim 14 wherein said semiconductor wafer comprises a silicon wafer.

19. The method as recited in claim 14 wherein said semiconductor wafer comprises at least one layer located on a silicon substrate.

20. The method as recited in claim 14 further comprising performing said energy dispersive spectroscopy on said area of interest at an energy.

* * * * *